United States Patent
Chen et al.

(10) Patent No.: US 11,662,286 B2
(45) Date of Patent: May 30, 2023

(54) SURVEY METHOD OF SOIL CARBON STOCK IN VEGETATED COASTAL WETLANDS

(71) Applicant: Third Institute of Oceanography, Ministry of Natural Resources of the People's Republic of China, Fujian (CN)

(72) Inventors: Guangcheng Chen, Xiamen (CN); Shunyang Chen, Xiamen (CN); Bin Chen, Xiamen (CN); Wenshuo An, Xiamen (CN); Weiwei Yu, Xiamen (CN)

(73) Assignee: THIRD INSTITUTE OF OCEANOGRAPHY, MINISTRY OF NATURAL RESOURCES OF THE PEOPLE'S REPUBLIC OF CHINA, Fujian (CN)

( * ) Notice: Subject to any disclaimer, the term of this patent is extended or adjusted under 35 U.S.C. 154(b) by 0 days.

(21) Appl. No.: 17/702,778

(22) Filed: Mar. 23, 2022

(65) Prior Publication Data

US 2022/0307958 A1    Sep. 29, 2022

(30) Foreign Application Priority Data

Mar. 24, 2021  (CN) .......................... 202110312912.2
Mar. 24, 2021  (CN) .......................... 202110314174.5

(51) Int. Cl.
*G01N 5/04* (2006.01)
*G01N 33/24* (2006.01)

(52) U.S. Cl.
CPC ............. *G01N 5/045* (2013.01); *G01N 33/24* (2013.01)

(58) Field of Classification Search
CPC ............................... G01N 5/045; G01N 33/24
See application file for complete search history.

(56) References Cited

FOREIGN PATENT DOCUMENTS

| CN | 101984353 A | * | 3/2011 |
|---|---|---|---|
| CN | 109669022 A | * | 4/2019 |
| CN | 111488902 A | * | 8/2020 |
| CN | 111781200 A | * | 10/2020 |
| CN | 112051363 A | * | 12/2020 |

* cited by examiner

*Primary Examiner* — Ryan D Walsh
(74) *Attorney, Agent, or Firm* — Leong C. Lei

(57) ABSTRACT

The disclosure relates to a survey method of soil carbon stock in vegetated coastal wetlands, which excludes the influence of plant's fine roots when estimating the soil carbon stock, and effectively avoids double counting organic carbon stock of the fine roots in soil carbon stock surveys. At the same time, this method does not require bulk density calculation, which reduces the influence of sample volume compression during sample processing when calculating bulk density and provides a more accurate survey method for the study of coastal wetland carbon stock.

1 Claim, No Drawings

SURVEY METHOD OF SOIL CARBON STOCK IN VEGETATED COASTAL WETLANDS

TECHNICAL FIELD

The disclosure relates to the field of surveying soil carbon stock of coastal wetland, in particular to a survey method of soil carbon stock in vegetated coastal wetlands covered by vegetation such as mangroves, salt marshes and seagrass beds.

BACKGROUND OF RELATED ARTS

In recent years, the issue of carbon stock has increasingly become a frontier and hot issue in the field of global change and geoscience research. Due to its rich carbon stock and strong carbon burial capacity, coastal wetlands have received extensive attention. Soil carbon stock is an important content of carbon stock in wetland ecosystems and the basic data for the establishment of greenhouse gas inventories in the country. Changes in soil carbon stock can reflect the carbon stock potential of wetlands. The spatial distribution and influencing factors of carbon stock and carbon burial potential are of great significance for protection of ecosystem carbon resources.

The general survey method of soil carbon stock in coastal wetlands is to stratify columnar samples after on-site collection, and then determining bulk density and carbon content by taking a small portion of samples from each layer. The carbon stocks of each layered sample and the entire column are calculated using the bulk density, the soil volume and the organic carbon content. Bulk density measurement generally uses a ring knife or a syringe to take a fixed volume of soil samples to measure the mass. The sampling and processing procedures cause problems such as secondary compression of the samples, thus reducing the accuracy of soil carbon stock estimation. Furthermore, current methods generally include the carbon stored in fine root biomass in the soil carbon stock calculations, leading to an overestimation of soil carbon stock. On the other hand, the carbon stock of coastal wetland ecosystems is generally divided into two parts: soil and vegetation. For those coastal wetlands with developed underground root systems and a large number of fine plant roots, the root system/fine root effects that are not considered when measuring soil carbon stock, can result in double counting of fine root carbon stock.

In view of this, the inventors have deeply conceived the problems occurring in the existing methods for surveying carbon stock of coastal wetland, and thus came up with this application.

SUMMARY

The purpose of the present disclosure is to provide a survey method of soil carbon stock in vegetated coastal wetlands, which can avoid the influence of plant roots in the soil and perform accurate estimation of the soil carbon stock in coastal wetlands.

To achieve the above object, the technical solution adopted in the present disclosure is:

A survey method of soil carbon stock in vegetated coastal wetlands, including:

step 1: collecting a soil sample of coastal wetland;
step 2: processing the soil sample;
layering the soil sample, and weighing the total wet weight $W_{total\ wet\ i}$ of each layer of the soil sample;

dividing each layer of the soil sample into two parts, removing thick roots, and then defining the two parts of the soil sample as sample 1 and sample 2 respectively; storing the thick roots picked out from each layer of the soil sample as a thick roots sample, and washing and drying the thick roots sample, and obtaining the wet weight $W_{thick\ roots\ i}$ of the thick roots of each layer of the soil sample;

weighing the wet weight $W_{1\ wet\ i}$ and the dry weight $W_{1\ dry\ i}$ of the sample 1, and then taking the soil sample without fine roots from the sample 1 after homogenizing the sample 1 for determining carbon content;

weighing the wet weight $W_{2\ wet\ i}$ of the sample 2, and then obtaining the fine roots in sediment by washing with water and sieving, and drying and weighing the weight $W_{fine\ roots\ i}$ of the fine roots;

step 3: analyzing and testing the samples;

measuring each layer of the soil sample without fine roots from the sample 1 by using an elemental analyzer to obtain soil carbon content $C_{Si}$ (mg/g as the unit), and the soil carbon content is organic carbon content, inorganic carbon content or total carbon content;

step 4. calculating soil carbon stock;

(a) calculating moisture content $W_{Ci}$ of each layer of the soil sample:

$$W_{Ci} = \frac{W_{1\ wet\ i} - W_{1\ dry\ i}}{W_{1\ wet\ i}} \times 100\%,$$

in this formula, $W_{1\ wet\ i}$ represents the wet weight of the sample 1 (g as the unit); $W_{1\ dry\ i}$ represents the dry weight of the sample 1 (g as the unit);

(b) calculating total dry weight $W_{dry\ i}$ of each layer of the soil sample:

$W_{dry\ i} = (W_{wet\ i} - W_{thick\ roots\ i}) \times W_{Ci}$, in this formula, $W_{wet\ i}$ represents the total weight of each layer of the soil sample (g as the unit), $W_{Ci}$ represents the moisture content of each layer of the soil sample (% as the unit), $W_{thick\ roots\ i}$ represents the total wet weight of each layer of the thick roots sample (g as the unit);

(c) calculating total weight $W_{TRi}$ of the fine roots of each layer of the soil sample:

$$W_{TRi} = \frac{W_{wet\ i} - W_{thick\ roots\ i}}{W_{2\ wet\ i}} \times W_{fine\ roots},$$

in this formula, $W_{wet\ i}$ represents the total weight of each layer of the soil sample (g as the unit); $W_{2\ wet\ i}$ represents the wet weight of the sample 2 (g as the unit); $W_{thick\ roots\ i}$ represents the total wet weight of each layer of the thick roots sample (g as the unit); $W_{fine\ roots\ i}$ represents the total dry weight of the fine roots of the sample 2 (g as the unit);

(d) calculating the total dry weight $W_{soil\ dry\ i}$ of the soil in each layer of the sample:

$W_{soil\ dry\ i} = W_{dry\ i} - W_{TRi}$, in this formula, $W_{dry\ i}$ represents the total dry weight of each layer of the samples (g as the unit); $W_{TRi}$ represents the total weight of each layer of the fine roots (g as the unit);

(e) calculating the soil carbon stock $TC_i$:

$$TC_i = \frac{W_{soil\ dry\ i} \times C_{Si}}{\pi \times \left(\frac{D}{2}\right)^2},$$

in this formula, $W_{soil\ dry\ i}$ represents the total dry weight of the soil in each layer of the soil sample (g as the unit); D represents the inner diameter of the collection tube (m as the unit); $C_{Si}$ represents the soil carbon content of each layer of the soil sample (mg/g as the unit);

(f) calculating the soil carbon stock TC:

$TC = \Sum_{i=1}^{n} TC_i$, $TC_i$ represents the soil carbon stock of each layer of the soil sample (g/m² as the unit); n represents the number of the layers of the soil sample.

After adopting the above scheme, when estimating the carbon stock in the present disclosure, the collected columnar soil sample is stratified and weighed, and then the sample 1 and the sample 2 are taken out from the sample per layer. The sample 1 is used to obtain the dry weight of the sample with fine roots and to determine the content of soil organic carbon/inorganic carbon/total carbon of the sample without fine roots, and the sample 2 is used to obtain the total mass of the fine roots in each layer of the sample. Then, the total weight of the fine roots is subtracted from to obtain the soil mass of the sample the total dry weight of each layer of the sample, and the stock of organic carbon/inorganic carbon/total carbon in the soil is further calculated; this method eliminates the influence of plant fine roots and also effectively avoids the double-counting problem of the organic carbon stock of the fine roots in the soil carbon stock survey, thereby providing a more accurate method for survey of the study of carbon stock of coastal wetland.

In addition, when the present disclosure performs sample processing, the wet weight of each layer of the samples will be weighed, and then the dry weight of each layer of samples will be calculated by using the moisture content and wet weight, which does not need to be calculated by bulk density, which reduces the sample processing process when measuring bulk density. The impact of the sample volume compression in the middle of the study improves the accuracy of soil carbon stock surveys in coastal wetlands, further improves the accuracy of soil carbon stock with fine roots, and ensures the accuracy of soil carbon stock.

DETAILED DESCRIPTIONS OF EMBODIMENTS

The disclosure provides a survey method of soil carbon stock in vegetated coastal wetlands, which includes as below.

Step 1. Collecting a Soil Sample of Coastal Wetland:

In this example, the columnar sample collection method is used to collect the soil of coastal wetlands, the sampling depth is 1 m, and the sampling tube is a PVC tube with an inner diameter (D) of 7 cm.

Sampling tools including the PVC tube (with one end for installing a custom cut head in order to help cut the root system), a hammer, a sealing cap of the PVC tube, a tape, a handle, a custom cut head, etc. are prepared.

When sampling, after recording the total length (L) of the PVC tube (can also be other types of collection pipes), the end of the PVC tube with the custom cut head is put downward, the custom handle is installed thereon, rotated into the soil, and a hammer is used for slowly hammering the upper section of the PVC tube until the PVC tube reaches the designed sampling depth.

Then, the depth (L1) of the PVC tube that presses into the soil and the length (L2) of the soil inside the PVC tube are recorded.

Next, the top of the PVC tube is covered by the sealing cap and sealed by the tape, and the custom handle is used to slowly pull out the PVC tube.

Finally, after pulling out the PVC tube, the bottom end of the PVC tube is sealed by the sealing cap to ensure that the sample does not to leak from the bottom of the PVC tube. The soil in the PVC tube is the soil sample.

Step 2. Processing the Soil Sample:

The soil sample should be sent back to the laboratory for processing as soon as possible after collection. The specific processing methods are as follows.

Step 2.1. The PVC tube is sawn along the side with a chainsaw to obtain a complete columnar soil sample; when using the chainsaw, the depth of the saw blade is adjusted with attention so that the PVC tube is sawed without damaging the sample in the tube, thereby reducing the impact of PVC powder on the soil sample.

Step 2.2. The actual length (L3) of the soil sample is recorded and the soil sampling compression rate is calculated using the formula $$\rho = \frac{L_3}{L_1 - (L_2 - L_3)}.$$

Step 2.3. The soil sample is layered according to the research needs, the theoretical layering depth is set as $H_{theoretical}$, and the actual layering depth (H) is calculated according to the sampling compression ratio ($\rho$):

$$H = H_{theoretical} \times \rho$$

In this example, $H_{theoretical} = 10$ cm.

Step 2.4. The sample is cut into layers according to the actual layer depth H, and the total wet weight $W_{total\ wet\ i}$ of each layer of the soil is weighed.

Step 2.5. Each layer of the sample is cut in half to be divided into two parts. After removing the thick roots, the inner soils (about 150 g, without the influence of PVC powder) is taken from the two parts respectively and the two parts are recorded as sample 1 and sample 2 respectively. The thick roots are removed from each layer of the sample to form a thick roots sample, the thick roots sample of each layer is washed and drained off surface moisture to obtain the wet weight $W_{thick\ roots\ i}$ of each layer of the thick roots;

Step 2.6. After weighing the wet weight $W_{1\ wet\ i}$ and dry weight $W_{1\ dry\ i}$ of each layer of the sample 1, the sample 1 is homogenized evenly and the soil sample is taken without the fine roots for the determination of carbon deposition; the wet weight $W_{2\ wet\ i}$ of each layer of the sample 2 is weighed, and then the fine roots in the soil is extracted by washing with water and sieving and drying to form a fine roots sample, and the fine roots sample is weighed $W_{fine\ roots\ i}$.

Step 3. Analyzing and Testing the Samples:

The soil sample of the sample 1 without the fine roots is air-dried at room temperature and then ground through a 100-mesh sieve, and the soil carbon content $C_{Si}$ is measured by an elemental analyzer, the unit is mg/g, and the soil carbon content is the organic carbon content, inorganic carbon content or total carbon content, wherein inorganic carbon=total carbon−organic carbon.

Step 4. Calculating Soil Carbon Stock:

(a) calculating moisture content $W_{Ci}$ of each layer of the soil sample:

$$W_{Ci} = \frac{W_{1\ wet\ i} - W_{1\ dry\ i}}{W_{1\ wet\ i}} \times 100\%,$$

in this formula, $W_{1\ wet\ i}$ represents the wet weight of the sample 1 (g as the unit); $W_{1\ dry\ i}$ represents the dry weight of the sample 1 (g as the unit);

(b) calculating total dry weight $W_{dry\ i}$ of each layer of the samples (including the fine roots):

$W_{dry\ i} = (W_{wet\ i} - W_{thick\ roots\ i}) \times W_{Ci}$, in this formula, $W_{wet\ i}$ represents the total weight of each layer of the samples (g as the unit); $W_{Ci}$ represents the moisture content of each layer of the soil sample (% as the unit) $W_{thick\ roots\ i}$ represents the total wet weight of each layer of the thick roots sample (g as the unit);

(c) calculating total weight $W_{TRi}$ of each layer of the fine roots:

$$W_{TRi} = \frac{W_{wet\ i} - W_{thick\ roots\ i}}{W_{2\ wet\ i}} \times W_{fine\ roots},$$

in this formula, $W_{wet\ i}$ represents the total weight of each layer of the soil sample (g as the unit); $W_{2\ wet\ i}$ represents the wet weight of the sample 2 (g as the unit); $W_{thick\ roots\ i}$ represents the total wet weight of each layer of the thick roots sample (g as the unit); $W_{fine\ roots\ i}$ represents the total dry weight of the fine roots of the sample 2 (g as the unit);

(d) calculating the total dry weight $W_{soil\ dry\ i}$ of the soil in each layer of the sample:

$W_{soil\ dry\ i} = W_{dry\ i} - W_{TRi}$, in this formula, $W_{dry\ i}$ represents the total dry weight of each layer of the samples (g as the unit); $W_{TRi}$ represents the total weight of each layer of the fine roots (g as the unit);

(e) calculating the soil carbon stock $TC_i$:

$$TC_i = \frac{W_{soil\ dry\ i} \times C_{Si}}{\pi \times \left(\frac{D}{2}\right)^2},$$

in this formula, $W_{soli\ dry\ i}$ represents the total dry weight of the soil in each layer of the soil sample (g as the unit); D represents the inner diameter of the collection tube (cm as the unit); $C_{Si}$ represents the soil carbon content of each layer of the soil sample (g/kg as the unit);

(f) calculating the soil carbon stock TC:

$TC = \Sigma_{i=1}^{n} = TC_i$, $TC_i$ represents the soil carbon stock of each layer of the soil samples (g/m² as the unit); n represents the number of the layers of the soil sample.

To sum up, the present disclosure divides the samples into layers (layering) when estimating the soil carbon stock in the coastal wetlands, and then the sample 1 and the sample 2 are taken out from the samples per layer. The sample 1 is used to obtain the dry weight of the sample with fine roots and to determine the content of soil organic carbon of the sample without fine roots, and the sample 2 is used to obtain the total weight of the fine roots. Then, the total weight of the fine roots is subtracted from the total dry weight of each layer of the sample including the fine roots to obtain the soil mass of the sample, and the stock of organic carbon/inorganic carbon/total carbon in the soil is further calculated; this method eliminates the influence of plant fine roots and also effectively avoids the double-counting problem of the organic carbon stock of the fine roots in the soil carbon stock survey, thereby providing a more accurate method for survey of the study of carbon stock of coastal wetland.

In addition, when the present disclosure performs sample processing, the wet weight of each layer of the samples will be weighed, and then the dry weight of each layer of samples will be calculated by using the moisture content and wet weight, which does not need to be calculated by bulk density, which reduces the sample processing process when measuring bulk density. The impact of the sample volume compression in the middle of the study improves the accuracy of soil carbon stock surveys in coastal wetlands, further improves the accuracy of soil carbon stock with fine roots, and ensures the accuracy of soil carbon stock.

The above are only the embodiments of the present disclosure, and do not limit the technical scope of the present disclosure. Therefore, any minor modifications, equivalent changes and modifications made to the above embodiments according to the technical essence of the present disclosure still belong to the present disclosure within the scope of the technical solution.

What is claimed is:

1. A survey method of soil carbon stock in vegetated coastal wetlands, comprising:

step 1: collecting a soil sample of coastal wetland;

step 2: processing the soil sample;

layering the soil sample, and weighing the total wet weight $W_{total\ wet\ i}$ of each layer of the soil sample;

dividing each layer of the soil sample into two parts, removing thick roots, and then defining the two parts of the soil sample as sample 1 and sample 2 respectively; storing the thick roots picked out from each layer of the soil sample as a thick roots sample, and washing and drying the thick roots sample, and obtaining the wet weight $W_{thick\ roots\ i}$ of the thick roots of each layer of the soil sample;

weighing the wet weight $W_{1\ wet\ i}$ and the dry weight $W_{i\ dry\ i}$ of the sample 1, and then taking the soil sample without fine roots from the sample 1 after homogenizing the sample 1 for determining carbon content;

weighing the wet weight $W_{2\ wet\ i}$ of the sample 2, and then obtaining the fine roots in sediment by washing with water and sieving, and drying and weighing the weight $W_{fine\ roots\ i}$ of the fine roots;

step 3. analyzing and testing the samples;

measuring each layer of the soil sample without fine roots from the sample 1 by using an elemental analyzer to obtain soil carbon content $C_{Si}$, mg/g as the unit, and the soil carbon content is organic carbon content, inorganic carbon content or total carbon content;

step 4. calculating soil carbon stock;

(a) calculating moisture content $W_{Ci}$ of each layer of the soil sample:

$$W_{Ci} = \frac{W_{1\ wet\ i} - W_{1\ dry\ i}}{W_{1\ wet\ i}} \times 100\%,$$

in this formula, $W_{1\ wet\ i}$ represents the wet weight of the sample 1, g as the unit; $W_{1\ dry\ i}$ represents the dry weight of the sample 1, g as the unit;

(b) calculating total dry weight $W_{dry\ i}$ of each layer of the samples:

$W_{dry\ i} = (W_{wet\ i} - W_{thick\ roots\ i}) \times W_{Ci}$, in this formula, $W_{wet\ i}$ represents the total weight of each layer of the samples, g as the unit; $W_{Ci}$ represents the moisture content of each layer of the soil sample, % as the unit; $W_{thick\ roots\ i}$ represents the total wet weight of each layer of the thick roots sample, g as the unit;

(c) calculating total weight $W_{TRi}$ of each layer of the fine roots:

$$W_{TRi} = \frac{W_{wet\,i} - W_{thick\,roots\,i}}{W_{2\,wet\,i}} \times W_{fine\,roots}, \qquad 5$$

in this formula, $W_{wet\,i}$ represents the total weight of each layer of the soil sample, g as the unit; $W_{2\,wet\,i}$ represents the wet weight of the sample 2, g as the unit; $W_{thick\,roots\,i}$ represents the total wet weight of each layer of the thick roots sample, g as the unit; $W_{fine\,roots\,i}$ represents the total dry weight of the fine roots of the sample 2, g as the unit;

(d) calculating the total dry weight $W_{soil\,dry\,i}$ of the soil in each layer of the sample:

$W_{soil\,dry\,i} = W_{dry\,i} - W_{TRi}$, in this formula, $W_{dry\,i}$ represents the total dry weight of each layer of the samples, g as the unit; $W_{TRi}$ represents the total weight of each layer of the fine roots, g as the unit;

(e) calculating the soil carbon stock $TC_i$:

$$TC_i = \frac{W_{soil\,dry\,i} \times C_{Si}}{\pi \times \left(\frac{D}{2}\right)^2},$$

in this formula, $W_{soil\,dry\,i}$ represents the total dry weight of the soil in each layer of the soil sample, g as the unit; D represents the inner diameter of a collection tube used for collecting the soil sample, in as the unit; $C_{Si}$ represents the soil carbon content of each layer of the soil sample, mg/g as the unit;

(f) calculating the soil carbon stock TC:

$TC = \Sigma_{i=1}^{n} TC_i$, $TC_i$ represents the soil carbon stock of each layer of the soil samples, g/m² as the unit; n represents the number of the layers of the soil sample.

* * * * *